(12) United States Patent
Chernomorsky et al.

(10) Patent No.: US 9,632,101 B2
(45) Date of Patent: Apr. 25, 2017

(54) SYSTEMS AND TRAYS FOR PROCESSING SAMPLES BY A ROBOTIC PLATFORM

(71) Applicant: Regeneron Pharmaceuticals, Inc., Tarrytown, NY (US)

(72) Inventors: Rostislav Chernomorsky, Bronx, NY (US); Nicholas Gale, Yorktown Heights, NY (US); Sam Cichon, Fishkill, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 497 days.

(21) Appl. No.: 14/151,627

(22) Filed: Jan. 9, 2014

(65) Prior Publication Data

US 2014/0196550 A1    Jul. 17, 2014

Related U.S. Application Data

(60) Provisional application No. 61/751,508, filed on Jan. 11, 2013.

(51) Int. Cl.
*B01L 3/00* (2006.01)
*G01N 37/00* (2006.01)
*G01N 35/00* (2006.01)

(52) U.S. Cl.
CPC ........ *G01N 35/0099* (2013.01); *B01L 3/5085* (2013.01); *B01L 2200/026* (2013.01); *B01L 2300/0609* (2013.01); *B01L 2300/0618* (2013.01); *B01L 2300/0681* (2013.01); *B01L 2300/0829* (2013.01); *B01L 2300/0851* (2013.01)

(58) Field of Classification Search
CPC ............... G01N 35/0099; B01L 3/5085; B01L 2200/026; B01L 2300/0609; B01L 2300/0681; B01L 2300/0829; B01L 2300/0851; B01L 2300/0618
USPC .......... 73/864.91, 61.55, 61.59, 863, 864.82, 73/964.83, 964.58

See application file for complete search history.

(56) References Cited

U.S. PATENT DOCUMENTS

| | | | |
|---|---|---|---|
| 4,828,386 | A | 5/1989 | Matkovich et al. |
| 5,141,718 | A | 8/1992 | Clark |
| 5,976,470 | A | 11/1999 | Maiefski et al. |
| 2003/0215940 | A1 | 11/2003 | Lacey et al. |
| 2006/0286003 | A1 | 12/2006 | Desilets et al. |
| 2008/0096270 | A1 | 4/2008 | Everett |
| 2010/0248213 | A1* | 9/2010 | Feiglin .................. B01L 3/5021 435/5 |

(Continued)

OTHER PUBLICATIONS

Internatioanl Search Report and Written Opinion for Application No. PCT/US2014/010887 dated May 8, 2014.

*Primary Examiner* — Clayton E LaBalle
*Assistant Examiner* — Warren K Fenwick
(74) *Attorney, Agent, or Firm* — Alston & Bird LLP

(57) ABSTRACT

A system for processing samples by a robotic platform has a tray that defines a well defining a drain. The well has a bottom surface, an access port in fluid communication with the drain, and an insert adapted to be received in the well. The insert has a bottom wall and a side wall. At least one of the bottom wall and the side wall define a plurality of openings, such that an interior of the insert is in fluid communication with the well when the insert is inserted into the well.

25 Claims, 16 Drawing Sheets

(56) References Cited

U.S. PATENT DOCUMENTS

2011/0091930 A1    4/2011  Vacanti et al.
2012/0208207 A1*  8/2012  Kolodkin ............ B01L 3/50255
                                                                    435/7.1

* cited by examiner

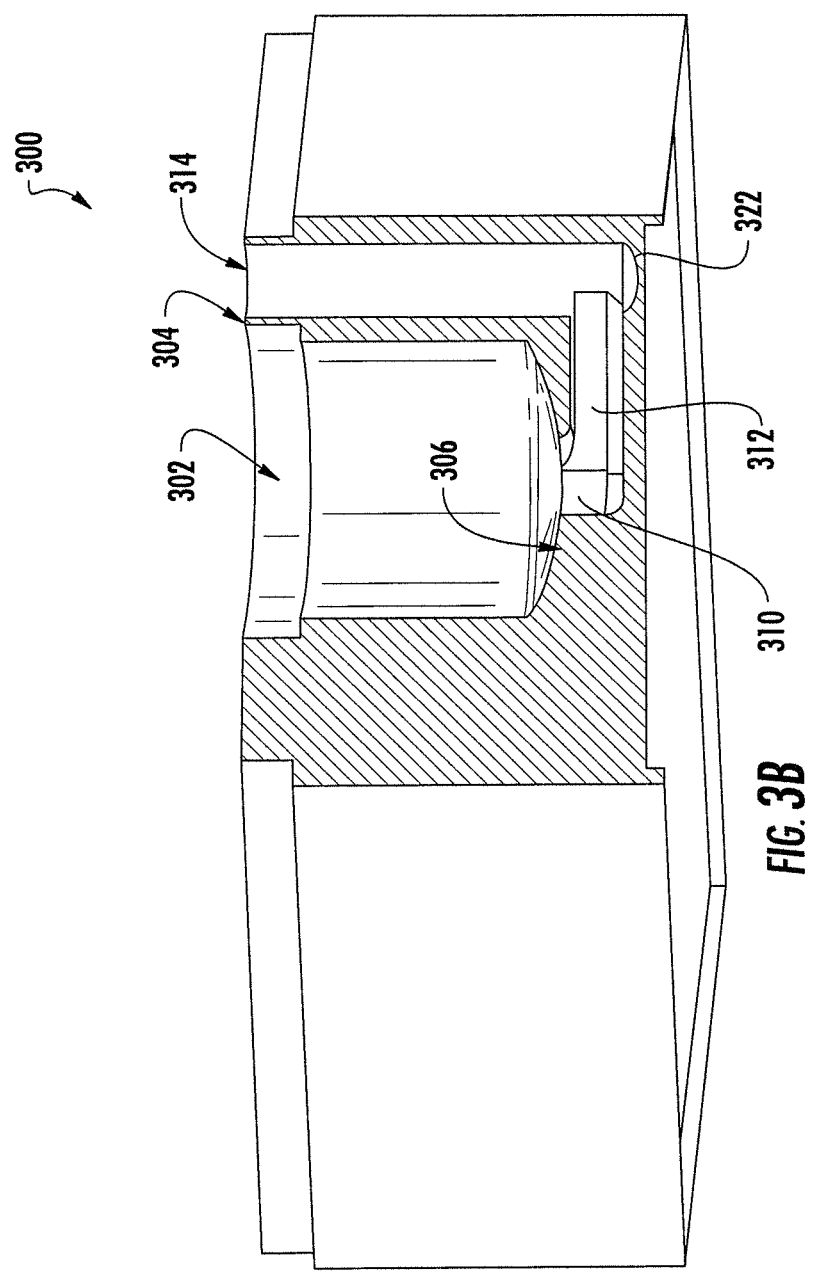

SYSTEMS AND TRAYS FOR PROCESSING SAMPLES BY A ROBOTIC PLATFORM

INTRODUCTION

Automated robotic processes are utilized extensively in laboratory settings to improve accuracy and reliability, as well as to improve processing times and to free operator resources for other tasks. Laboratory robots are often used to dispense multiple liquids with pipettes or other equipment configured to dispense and collect liquids of virtually any volume. These liquids may be deposited to and drawn from a number of sample wells which may contain cells, tissues, chemicals, biological agents, slides containing cells or tissues, or other material being tested. The liquids may be, or may include, tissue culture medium, reagents, wash fluid, dyes, or other chemicals, any or all of which may react in one way or another with the sample contained within the well. Individual samples may be contained within the wells of a microtiter plate, which may be transported as needed by the robotic equipment. Microtiter plates typically include 6, 12, 24, 96, 384 or more wells.

SUMMARY

In one aspect, the technology relates to a system for processing samples by a robotic platform, the system having: a tray defining: a well defining a drain, wherein the well has a bottom surface; and an access port in fluid communication with the drain; an insert adapted to be received in the well, wherein the insert includes a bottom wall and a side wall, wherein at least one of the bottom wall and the side wall define a plurality of openings, such that an interior of the insert is in fluid communication with the well when the insert is inserted into the well. In an embodiment, the well defines a channel connecting the drain and the access port, wherein the channel is pitched downward from the drain to the access port. In another embodiment, the bottom surface defines the drain. In yet another embodiment, the bottom surface has a high point and a low point, and wherein the drain is located proximate the low point. In still another embodiment, the low point is located proximate a center of the bottom surface.

In another embodiment of the above aspect, the low point is located proximate an outer edge of the bottom surface. In an embodiment, the well has an outer wall, and wherein the outer wall at least partially defines the drain. In another embodiment, the bottom surface defines a top surface of the channel. In yet another embodiment, the bottom surface at least partially defines an edge of the channel. In still another embodiment, the tray defines a slot, wherein the slot provides fluid communication between the well and the access port.

In another embodiment of the above aspect, the slot is configured to receive a gate. In an embodiment, the well includes an outer wall, and wherein when inserted into the well, the basket forms an interference fit with the outer wall. In another embodiment, at least one of the outer wall and the basket includes a gasket, wherein the gasket forms the interference fit. In yet another embodiment, the tray further has at least one of a clamp or a latch for securing the basket within the well. In still another embodiment, both of the bottom wall and the side wall define a plurality of openings.

In another embodiment of the above aspect, the well has an outer wall, wherein the outer wall defines at least one of a circular shape, a quadrilateral shape, an oval shape, and a triangular shape. In an embodiment, the side wall of the basket defines a shape complementary to the outer wall shape. In another embodiment, the tray defines a plurality of wells and wherein the access port is in fluid communication with at least two of the plurality of wells. In yet another embodiment, at least one of the plurality of openings has a sharp corner. In still another embodiment, at least one of the plurality of openings define an angle relative to the sidewall.

In another aspect, the technology relates to a tray for processing samples by a robotic platform, the tray having: a well defining a geometric shape having at least one outer wall and a bottom surface; an access port discrete from and in fluid communication with the well; and a basket configured to fit within the well, wherein the basket defines at least one side wall and a bottom wall, and wherein at least one of the side wall and bottom wall define a plurality of openings. In an embodiment, the well defines a drain defined by at least one of the outer wall and the bottom surface. In another embodiment, the bottom surface is at least one of substantially convex and substantially concave. In yet another embodiment, the bottom surface is sloped toward the outer wall. In still another embodiment, the tray further includes a channel connecting the well to the access port, wherein the channel is located below the bottom surface.

In another embodiment of the above aspect, the bottom surface at least partially defines the channel. In an embodiment, the tray includes a plurality of wells and the access port is in fluid communication with at least two of the plurality of wells.

BRIEF DESCRIPTION OF THE DRAWINGS

There are shown in the drawings, embodiments which are presently preferred, it being understood, however, that the technology is not limited to the precise arrangements and instrumentalities shown.

FIGS. 1A-3A are top perspective views of trays.
FIG. 3B is a partial side sectional view of a well in the tray of FIG. 3B.

DETAILED DESCRIPTION

Figure 1A:
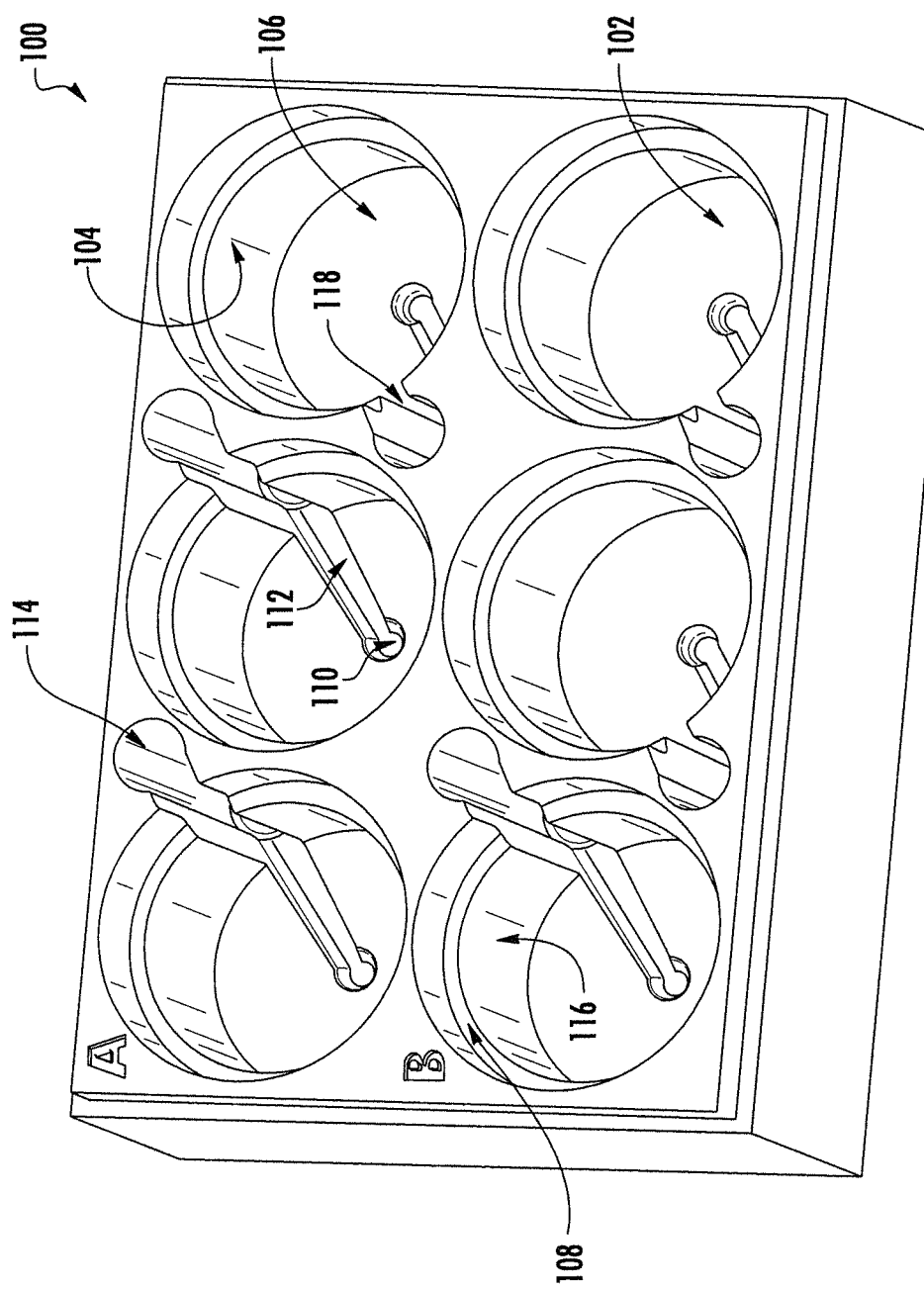
Figure 1B:
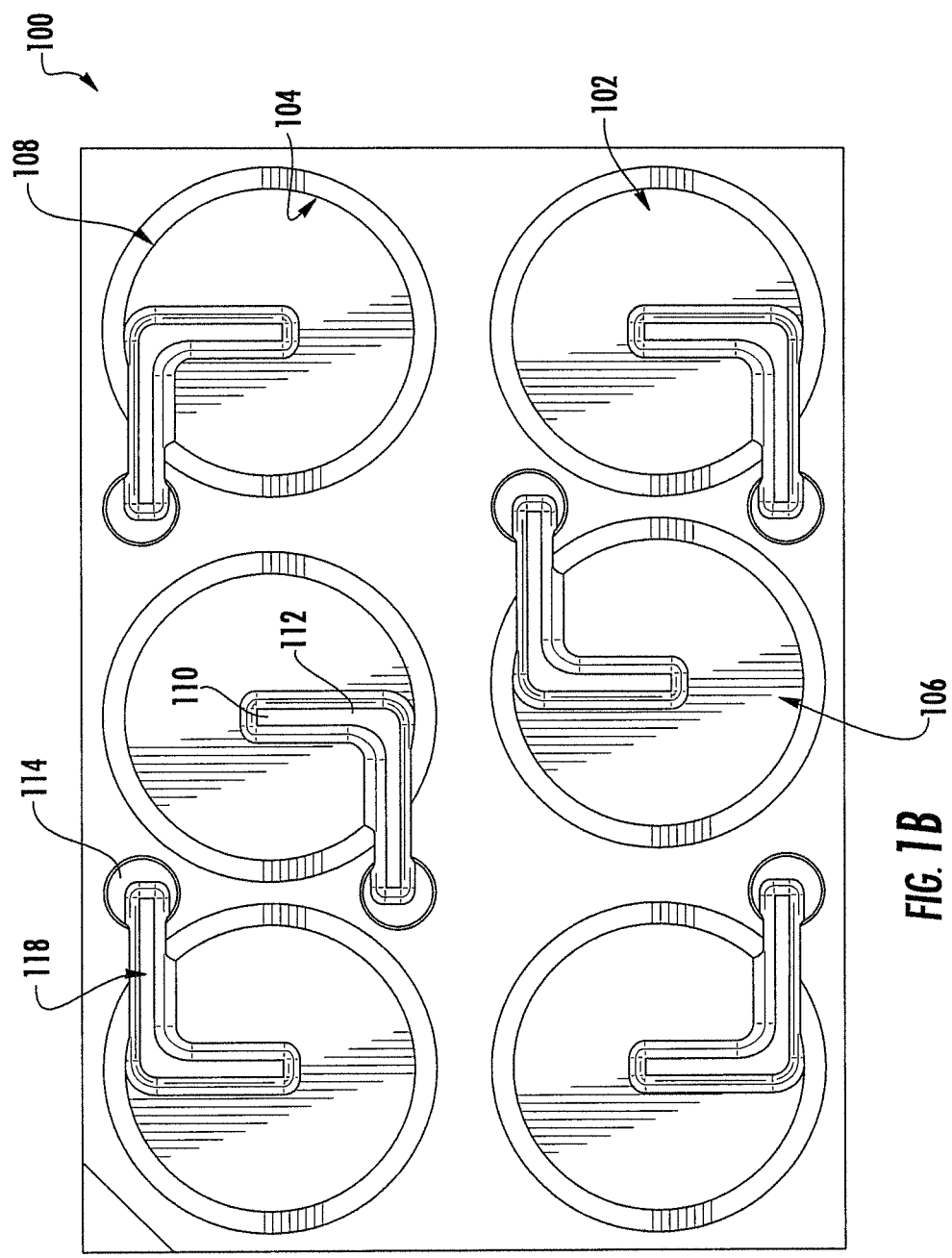

FIGS. 1A and 1B each depict six-well trays for use in biological sample processing. In FIG. 1A, the tray 100 defines six wells 102, each having an outer wall 104 and a bottom surface 106. The outer wall 104 may also define a rim 108 at an upper edge of the well 102. The rim 108 may be smooth, tapered, or threaded as required or desired to accommodate a particular mating basket (various types of which are described below). The bottom surface 106 defines a drain 110, centrally located in and defined by the bottom surface 106. A channel 112 connects the drain 110 to an access port 114. The access port 114 is sized and configured so as to receive a pipette. In general, a bottom surface of the access port 114 is located below a bottom surface of the drain 110, thus allowing any fluid in the channel 112 to drain passively towards the access port 114. The bottom surface 106 intersects the outer wall 106 at a corner 116. The bottom surface 106 pitches downward from the corner 116 to the drain 110. Accordingly, fluid located in the well 102 drains from the high point of the bottom surface 106 (in this case, the corner 116) to the low point of the bottom surface 106 (in this case, the drain 110), then down the slope of the channel 112 to the access port 114. In this tray 100, the well 102 and access port 114 are connected via a slot 118 that penetrates the outer wall 104 of the well 102. Advantages of this slot 118 include an increase in flow rate between the well 102 and the access port 114 (for example, when the pipette is inserted into the access port 114 to deliver fluid to or withdraw fluid from the well 102).

FIG. 1B depicts another embodiment of a tray 100. In this figure, elements having reference numbers similar to elements identified in FIG. 1A are generally the same as those previously-identified elements, unless otherwise noted. Notably, in the embodiment of FIG. 1B, the channel 112 is routed along an initial orientation substantially orthogonal to the outer wall 104. Once proximate the outer wall 104, the channel 112 turns about 90 degrees, then continues to the access port 114. As with the previous embodiment, the bottom surface 106 is convex, while the channel 112 slopes downward from the drain 110 to the access port 114. As can be seen from comparing the embodiments of FIGS. 1A and 1B, the routing of the channel 112 may be in any orientation from the drain 110 to the access port 114.

Figure 2A:
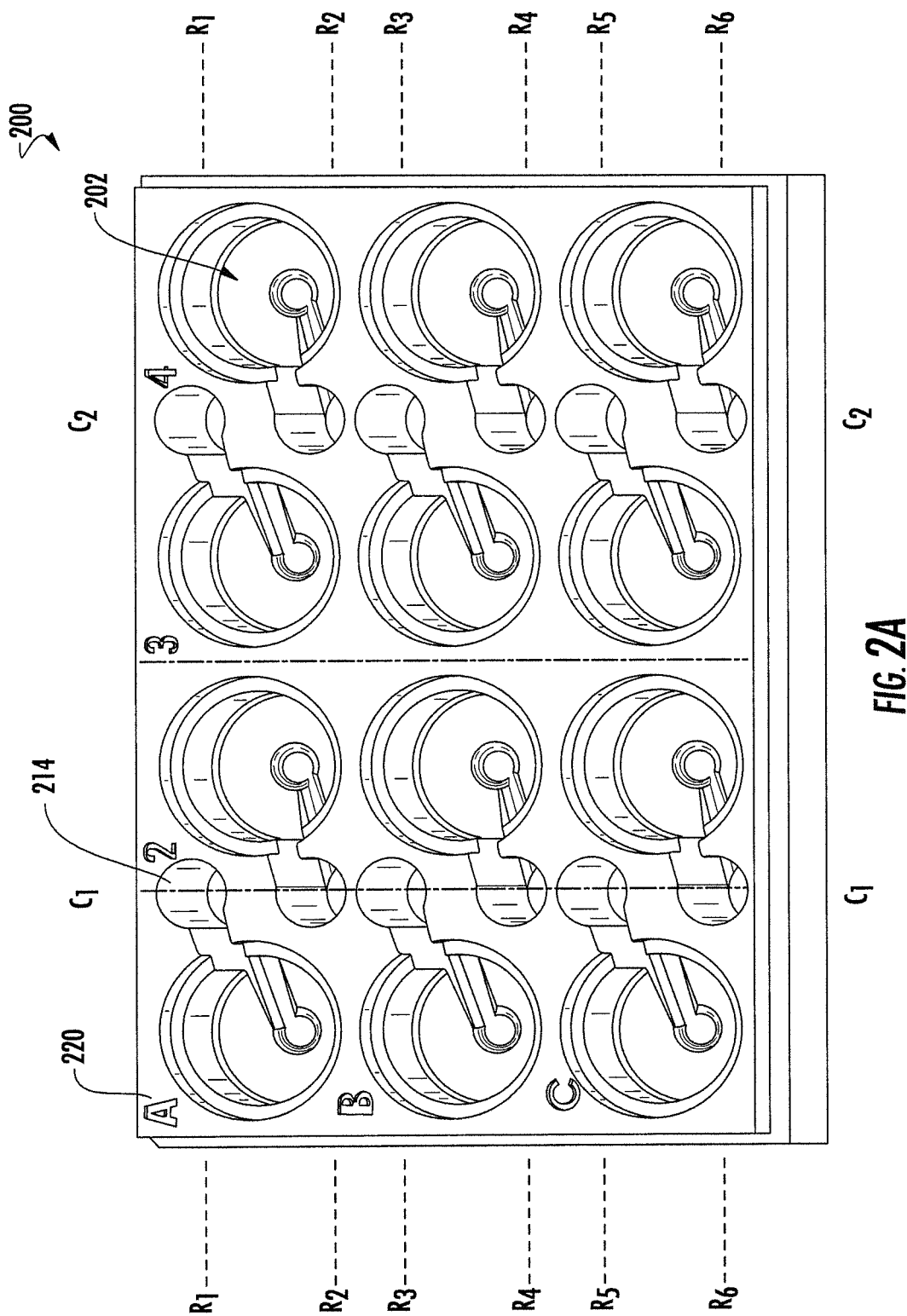
Figure 2B:
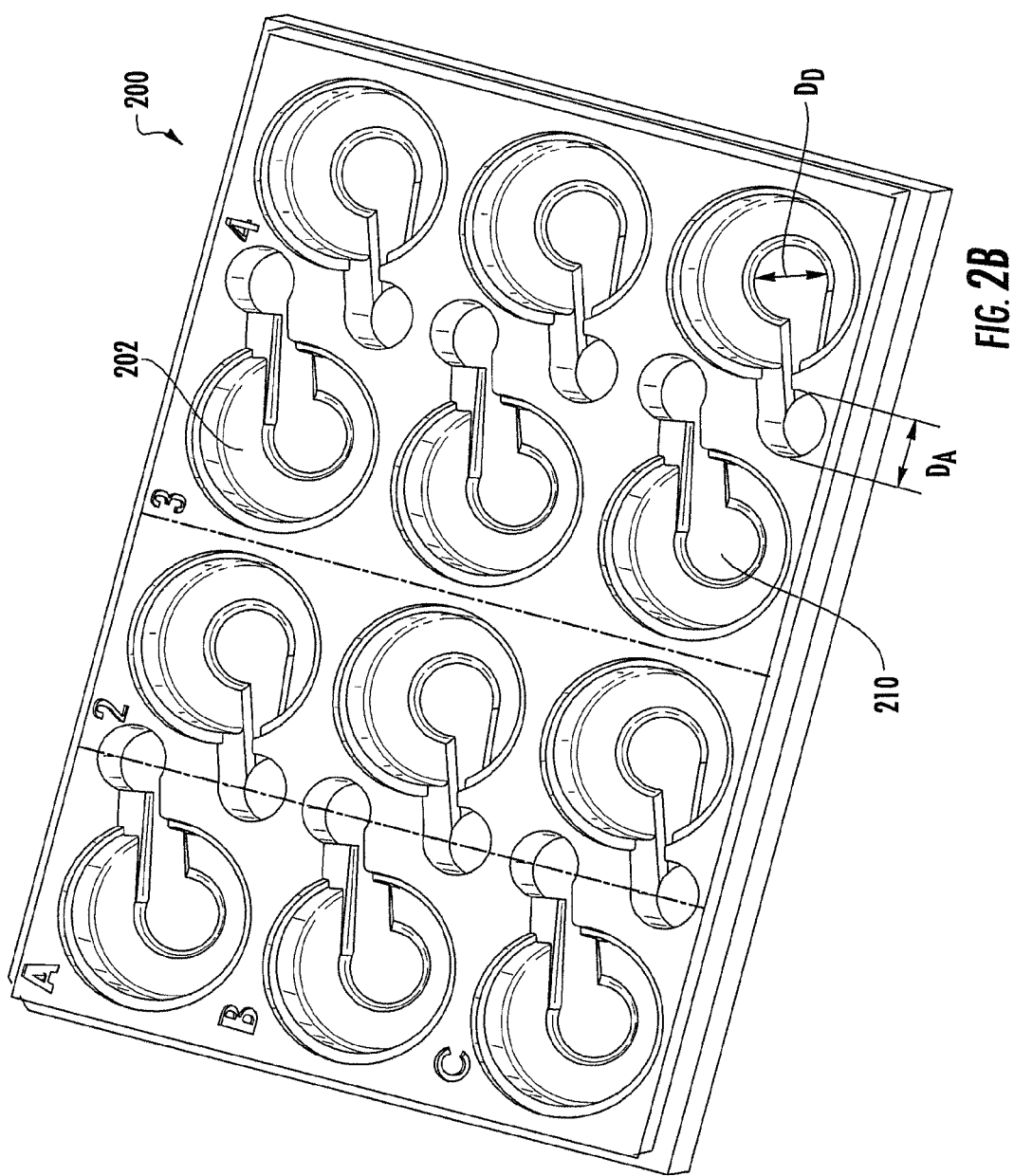

FIGS. 2A and 2B depict two embodiments of twelve-well trays 200 for use in biological liquid processing. Elements identified with reference numerals similar to those of the embodiments of FIG. 1A are generally the same as those previously-identified elements. Alignment of the access ports 214 is noticeable in this embodiment. The access ports 114 are aligned at two columns $C_1$ and $C_2$, as well as along six rows $R_1$-$R_6$. Configuration of the tray 200 such that the access ports 214 are so aligned allows a multi-pipette instrument to be used efficiently to introduce fluid to and withdraw fluid from the wells 202. Additionally, the tray 200 of FIG. 2A includes indicia 220, which may be used to identify a particular well by identifying its associated row and column.

FIG. 2B depicts a tray 200 having a well 202 with a drain 210 and channel 212. The previous embodiments of FIGS. 1A-2A depicted drains 110 that were smaller in diameter than the access ports 114. In the embodiment of FIG. 2B, however, the drain 210 has a drain diameter $D_D$ that is larger than the access port diameter $D_A$. This larger drain diameter $D_D$ allows for higher fluid flows through the drain 214. This larger drain helps reduce fluid turbulence during procedures, as well as fill time and drain time. It also reduces basket float as fluid is introduced.

Figure 3A:
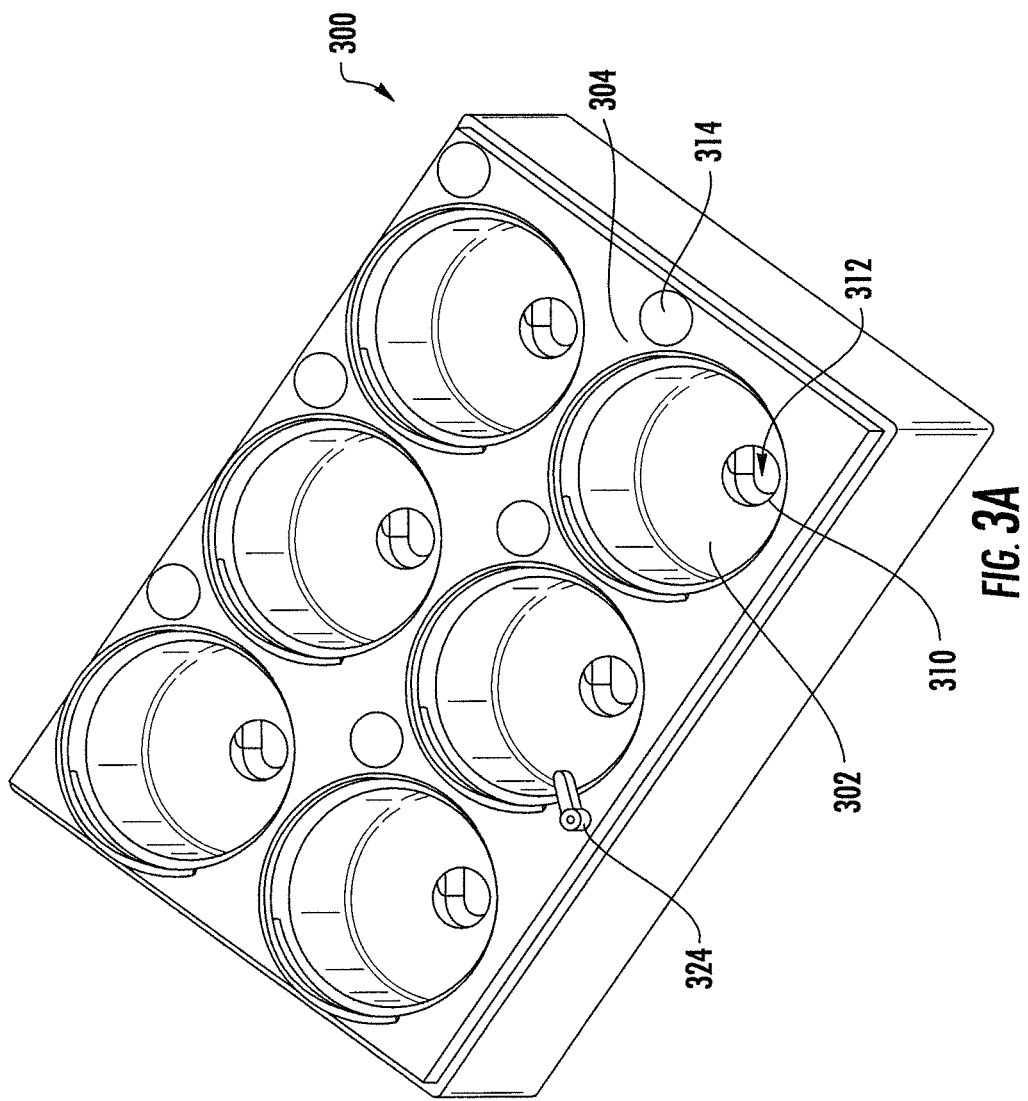

FIGS. 3A and 3B depict a tray 300 for use in biological liquid processing. Elements identified with reference numerals similar to those of the embodiments of FIG. 1A are generally the same as those previously-identified elements. A notable difference between the tray 300 and the previously-described trays is that the access port 314 is discrete from the well 302. Here, the outer wall 304 of the well 302 is unbroken. Thus, regardless of the rate of fluid introduction to or withdrawal from the access port 314, all fluid will enter the well 302 via the channel 312 (in the previously depicted embodiments, very high flow rates may cause fluid to flow through the slots depicted above). As depicted in FIG. 3B, the channel 312 is pitched downward from the drain 310 to the access port 314. In certain embodiments, the pitch may be between about 2 degrees to about 5 degrees. This helps facilitate draining of the well 302, as does the convex bottom surface 306 of the well 302. Additionally, a bottom portion 322 of the access port 314 is lower than the channel 312, which helps ensure that all fluid may be drawn out of the well (without any significant amounts remaining in, e.g., the channel 312). One or more of the wells 302 may be associated with one or more clamps, latches, or other locking elements 324 that may be used to secure a basket within the well 302.

Figure 4:
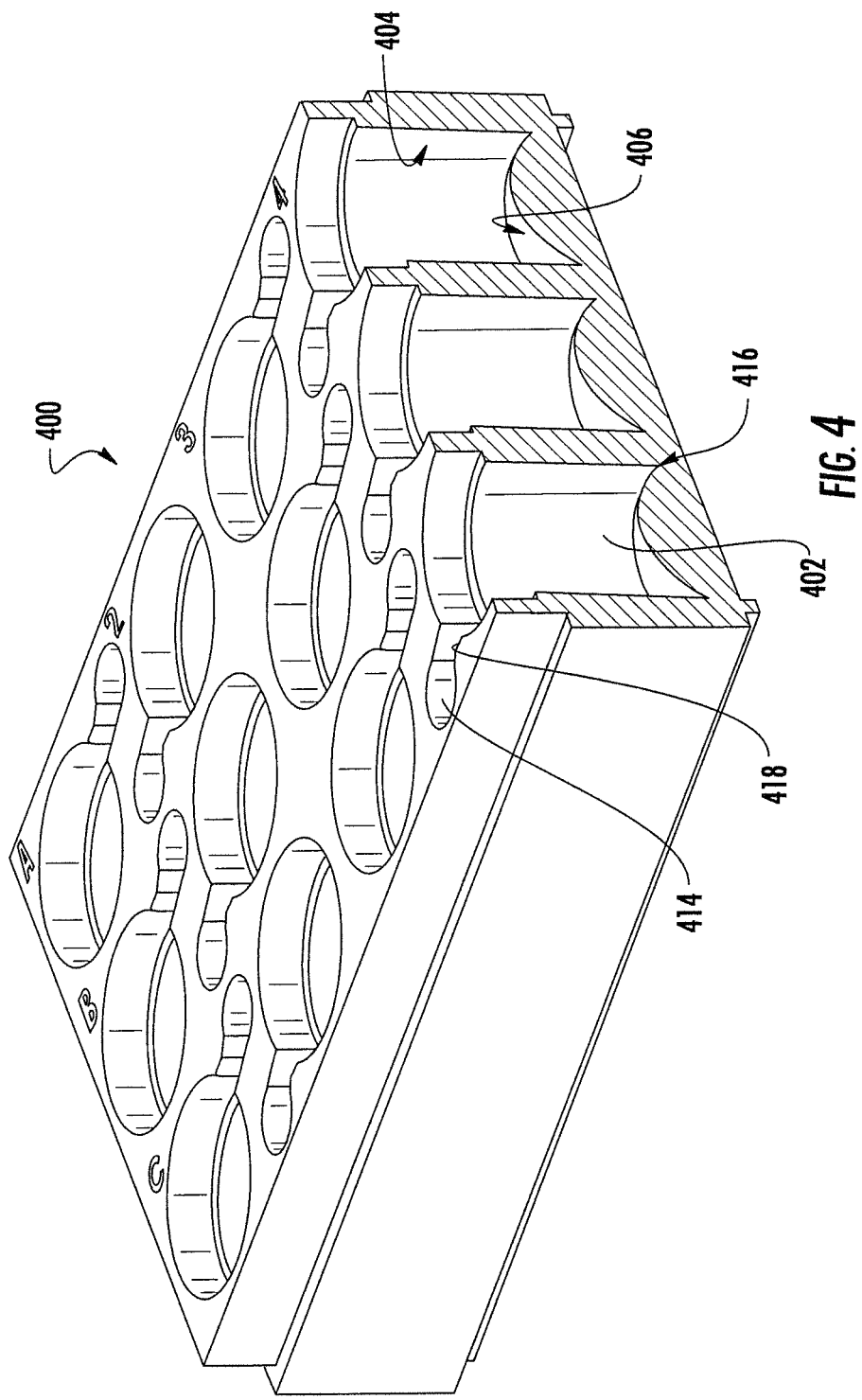
FIG. 4 is a perspective sectional view of a tray.

FIG. 4 depicts a perspective sectional view of another embodiment of a tray 400. In this embodiment, the bottom surface 406 of each well 402 is a convex configuration, which helps reduce basket float and improves drainage of the well 402. Accordingly, fluid within the well 402 drains from a center of the well 402 toward the outer wall 404. The corner 416 may be pitched from a high point to a low point at the outer perimeter of the bottom surface 406. A drain (not shown) is located at the low point. In certain embodiments, the drain need not be a discrete element, but may be the slot 418 that connects the access port 414 to the well 402.

Figure 5:
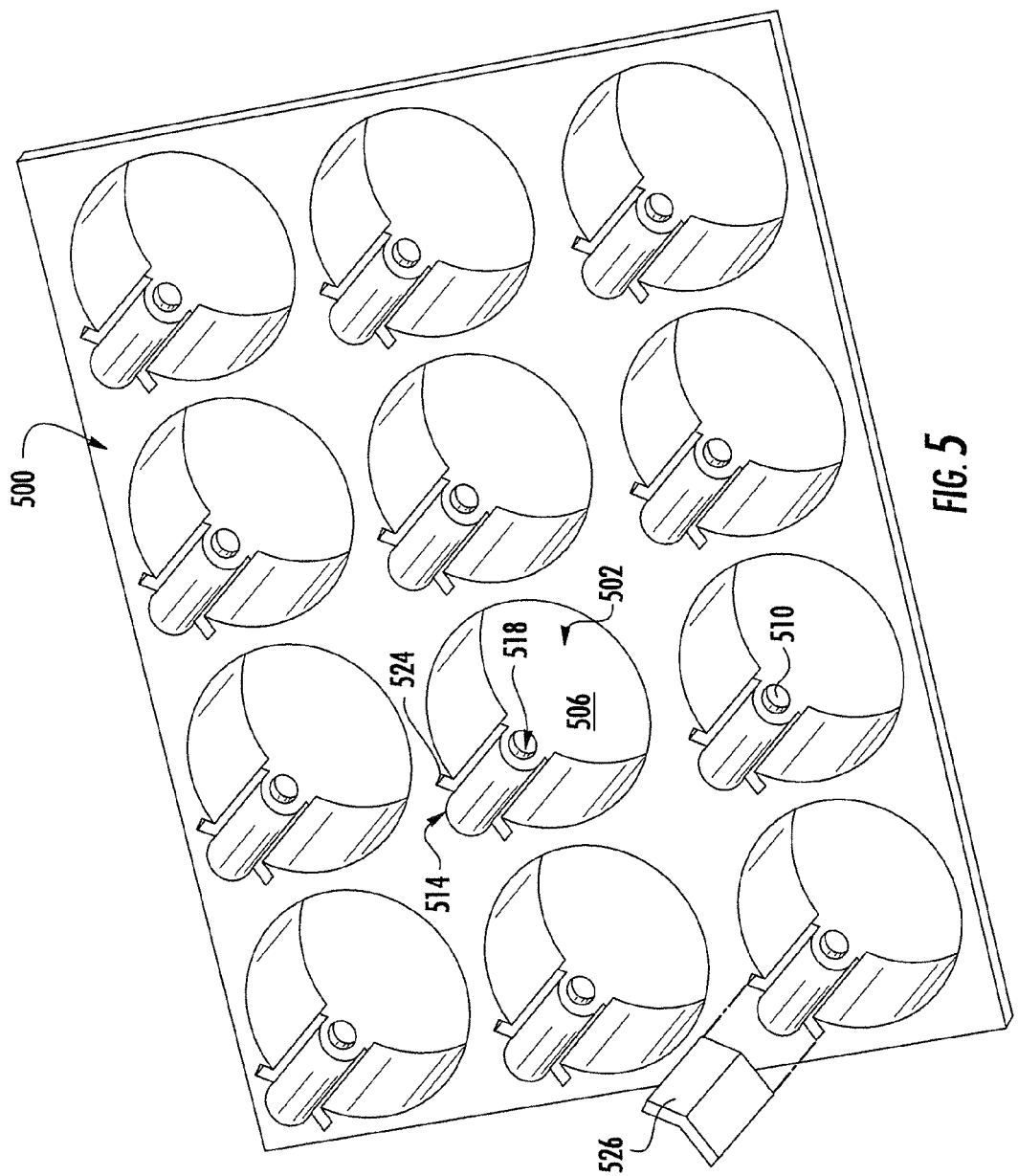
FIG. 5 is a top perspective view of another tray.

FIG. 5 depicts another embodiment of a tray 500. In this embodiment, an access port 514 is located very close to, and entirely in fluid communication with a well 502, via a slot 518. A drain 510 in this case is a low point of the access port 514, and the bottom surface 506 is pitched towards the access port 514 and the drain 510. Accordingly, in this embodiment, a pipette is inserted into the access port 514 and withdraws fluid from the drain 510, which receives the fluid contents of the well 502 due to the slope of the bottom surface 506. The slot 518 may further define one or more channels or receivers 524 for receiving a gate 526. The gate 526 may be received completely or partially within the receivers 524 so as to partially or completely isolate the well 502 from the access port 514, as required or desired for a particular application. Gaskets or other leak prevention devices may be utilized at the interface of the gate 526 and either or both of the receivers 524 and the bottom surface 506 to prevent unwanted leakage between the access port 514 and the well 502. Accordingly, a bottom edge of the gate 526 may be positioned above the bottom surface 506 so as to act as a flow control element between the access port 514 and the well 502.

Figure 6:
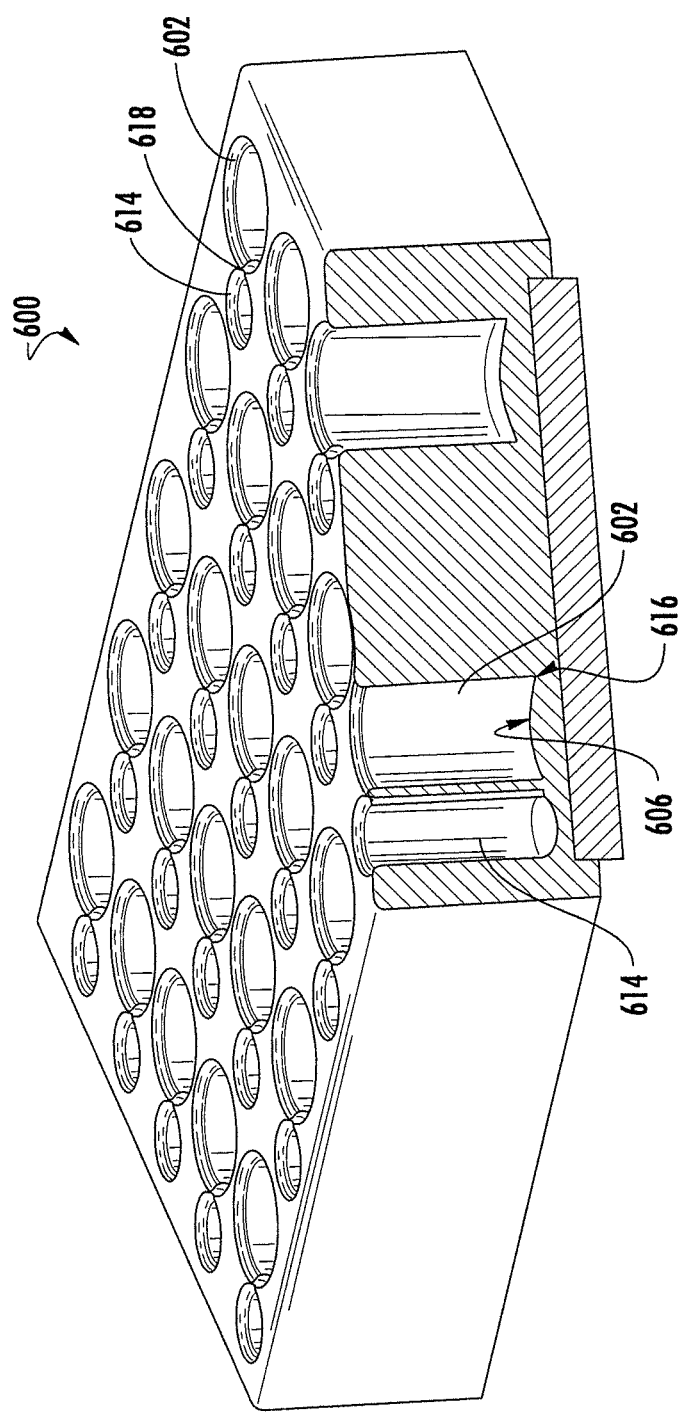
FIG. 6 is a perspective sectional view of another tray.

FIG. 6 depicts a perspective sectional view of another embodiment of a tray 600. In this embodiment, the bottom surface 606 of each well 602 is a convex configuration, which helps reduce basket float and improves drainage of the well 602. Accordingly, fluid within the well 602 drains from a center of the well 602 toward the outer wall 604. The corner 616 may be pitched from a high point to a low point at the outer perimeter of the bottom surface 606. A drain, in this case, a slot 618 connects the access port 614 to the well 602. The bottom of the access port 614 is concave, and therefor lower than the bottom surface 606 of its associated well 602, which helps improve draining.

Figure 7:
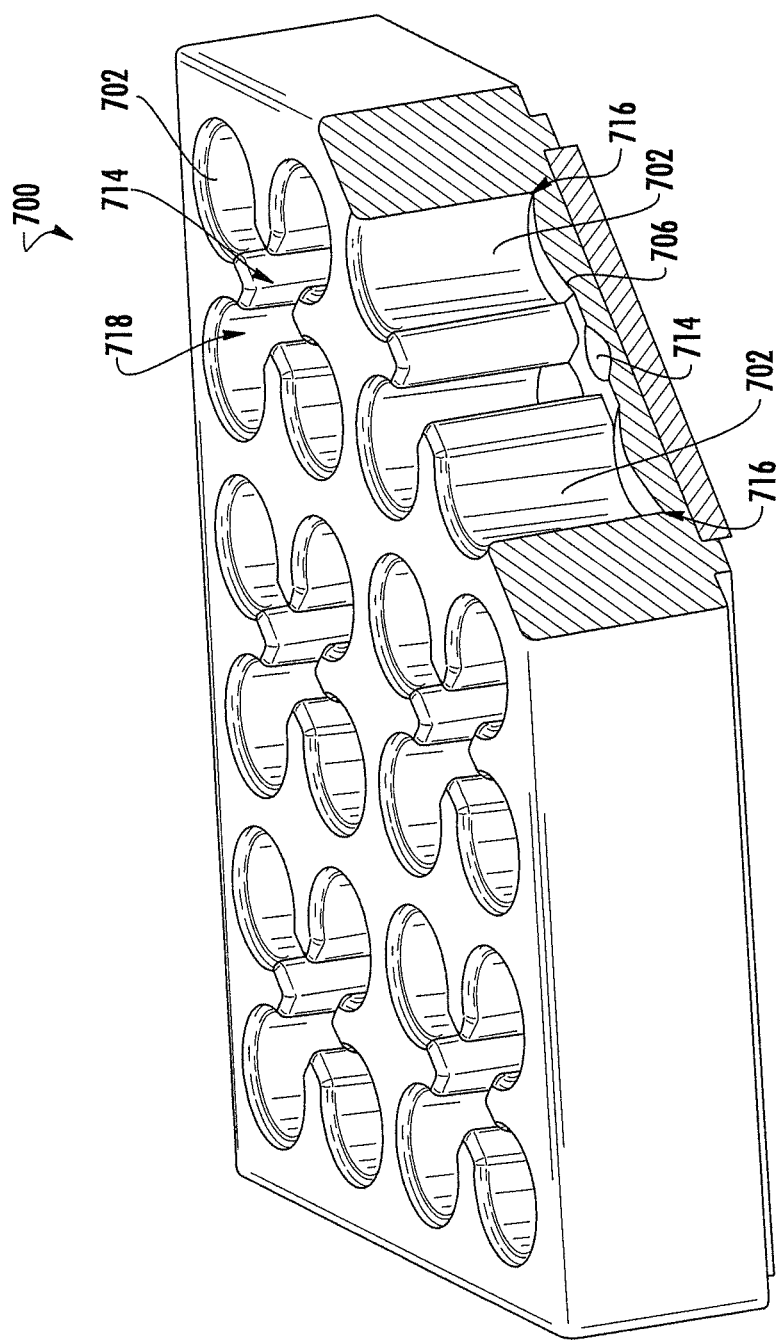
FIG. 7 is a perspective sectional view of another tray.

FIG. 7 depicts a perspective sectional view of another embodiment of a tray 700. In this embodiment, multiple wells 702 are served by a single access port 714. As with the embodiment of FIG. 6, the bottom surface 706 of each well 702 is a convex configuration, which helps reduce basket float and improves drainage of the well 702. Accordingly, fluid within the well 702 drains from a center of the well 702 toward the outer wall 704. The corner 716 may be pitched from a high point to a low point at the outer perimeter of the bottom surface 706. Drains, in this case, slots 718 connect the access port 714 to each of the wells 702. The bottom of the access port 714 is concave, and therefor lower than the bottom surface 706 of its associated wells 702, which helps improve draining. Although four wells 702 are depicted in communication with a single access port 714, greater or fewer than four wells may be in fluid communication with a single access port, as required or desired for a particular application. In general, multiple wells may be drained and filled via a single access port when cross-contamination of the contents of the multiple wells is not a concern.

Figure 8A:
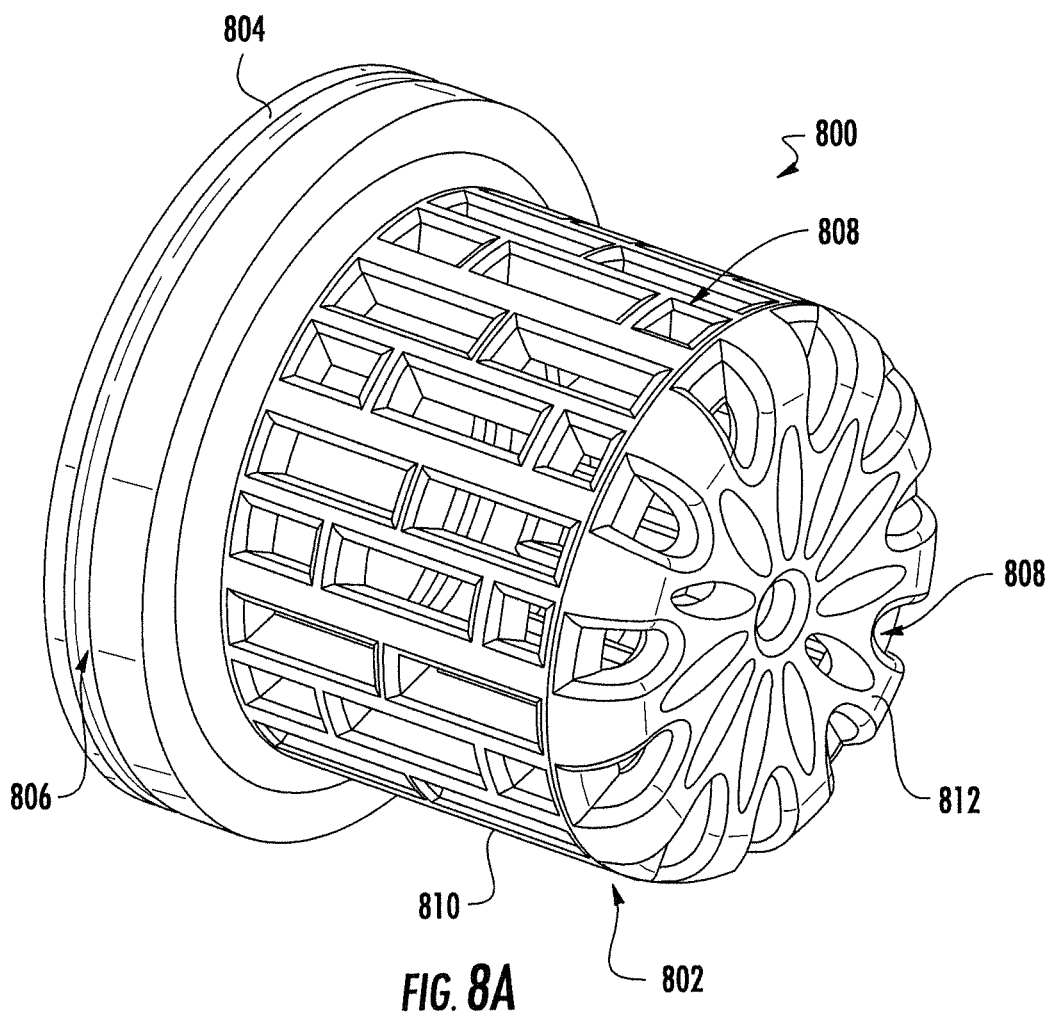
FIGS. 8A and 8B are perspective and perspective sectional views, respectively, of a sample basket.
Figure 8B:
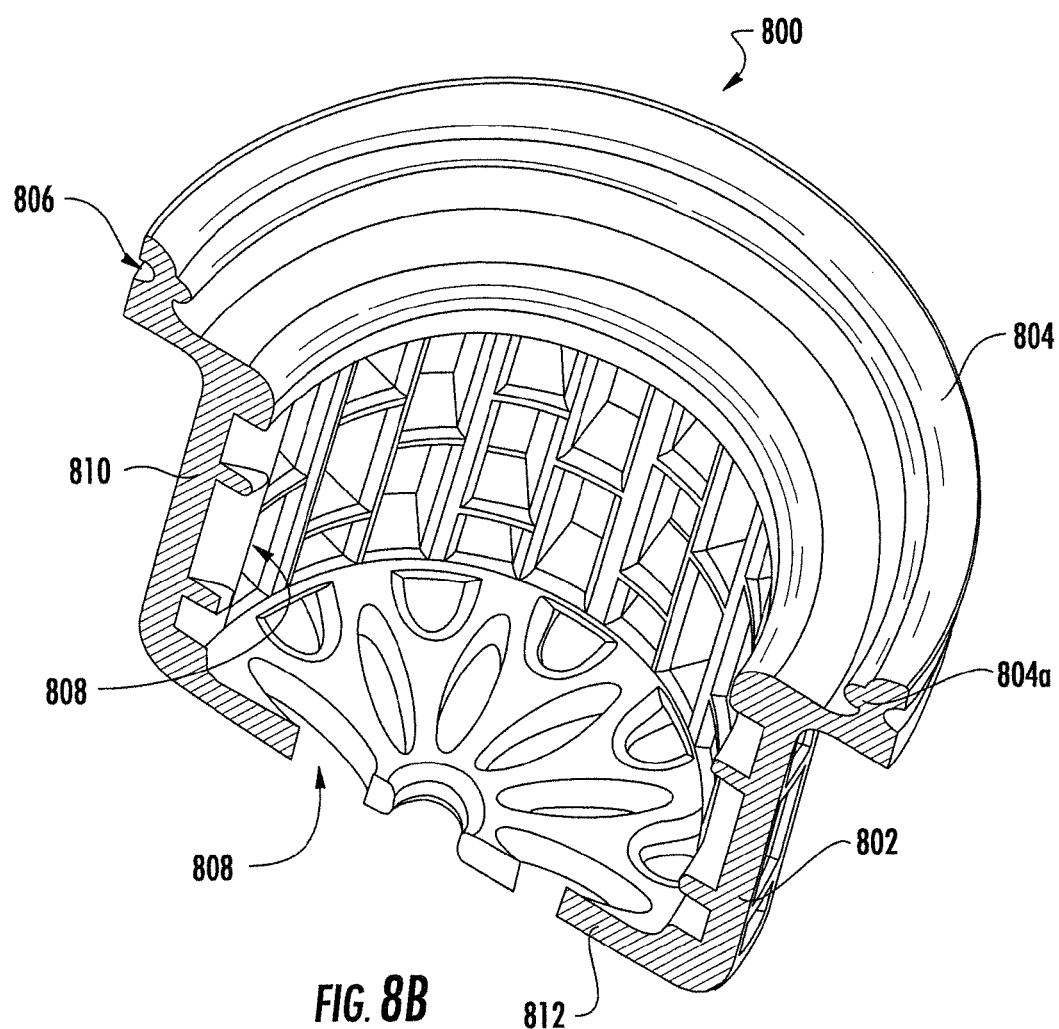

FIGS. 8A and 8B depict one embodiment of a sample insert or basket 800 that includes a container portion 802 and a lip 804. The lip 804 may include a groove 806 for receiving a gasket that may be used to secure the basket 800 when inserted into a well of a tray (such as the wells and trays described above). Interference between the rim of the well and the gasket forms an interference fit which prevents the basket 800 from being dislodged from the well during processing. Alternatively, the lip 804 itself may be manufactured of a resilient material to form an interference fit with the rim of the well, in the lieu of a discrete gasket or O-ring. Alternatively, mechanical securement elements, such as clamps, levers, hasps, etc. may be utilized to retain the basket 800 in the well. In certain embodiments, the lip may be threaded to mate with a corresponding thread on the rim of the well. Additionally, a mask or seal may be secured to a top surface of the tray to secure the basket, as well as prevent liquids from inadvertently sloshing out of the well during transport. In inner surface 804a of the lip 804 helps prevent sloshing and aids in removal of the basket 800 from its associated well.

The container portion 802 of the basket 800 defines a number of holes, openings, or penetrations 808 in both a sidewall 810 and bottom wall 812 thereof. The penetrations 808 may define any shape or size, as required or desired for a particular application. The penetrations 808 should be large enough to enable a high flow rate therethrough, but small enough to prevent the sample located within the basket 800 from escaping. It has been determined that baskets that include openings over a significant portion of the sidewall and bottom wall allow for improved flow rates over systems that utilize other structures to allow fluid introduction into a well (for example, systems having wells that utilize a mesh bottom surface). Baskets that have high flow rates allow the well to be filled quickly without dislodging the basket, as baskets that do not allow for adequate flow therethrough can dislodge from the associated well. Additionally, baskets that define holes having sharp corners (e.g., such as the rectangular holes in FIGS. 8A and 8B) help break the surface tension of higher viscosity liquids. This enables more fluid flow and helps reduce or eliminate basket float. Some or all of the holes may also define an angle relative to the sidewall or bottom wall of the basket so as to induce a current or swirl in the fluid to prevent samples from sticking therein.

Figure 9A:
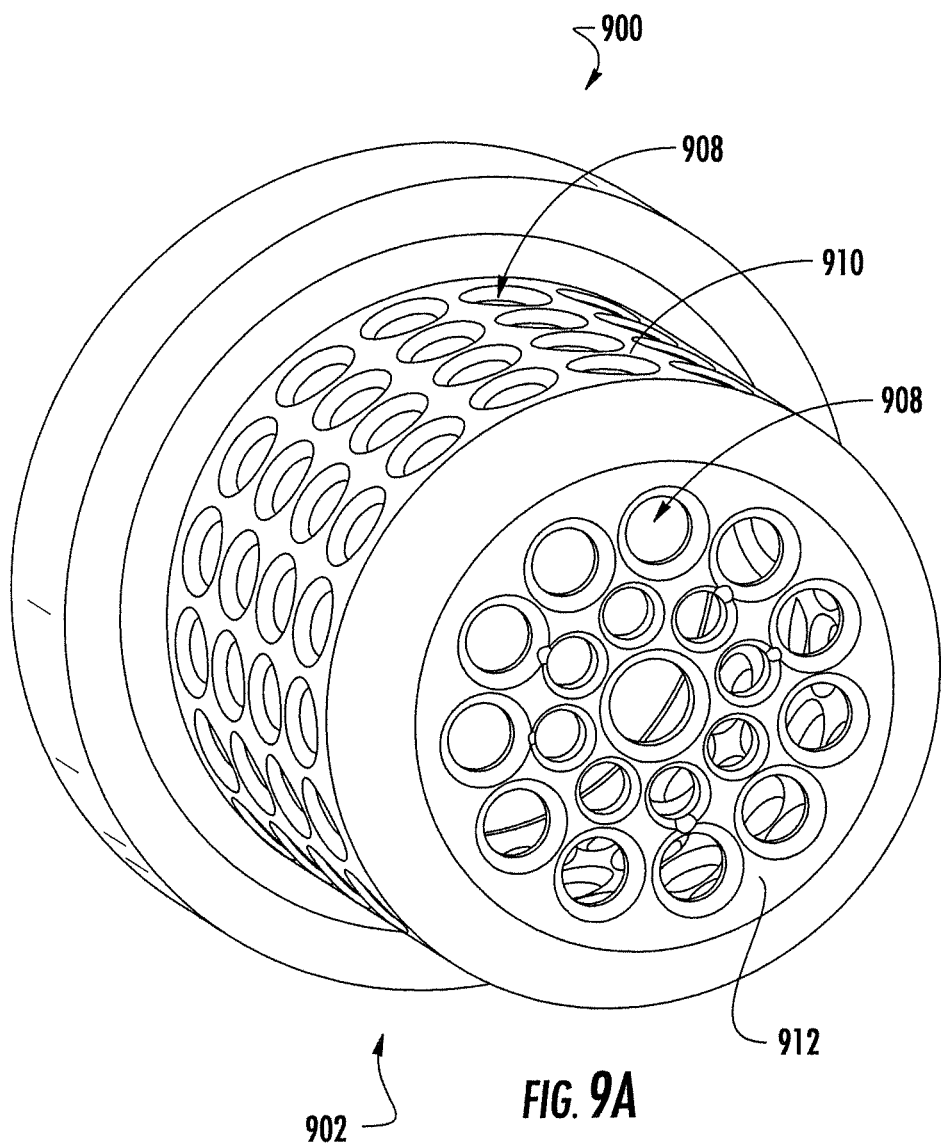
FIGS. 9A and 9B are perspective views of sample baskets.
Figure 9B:
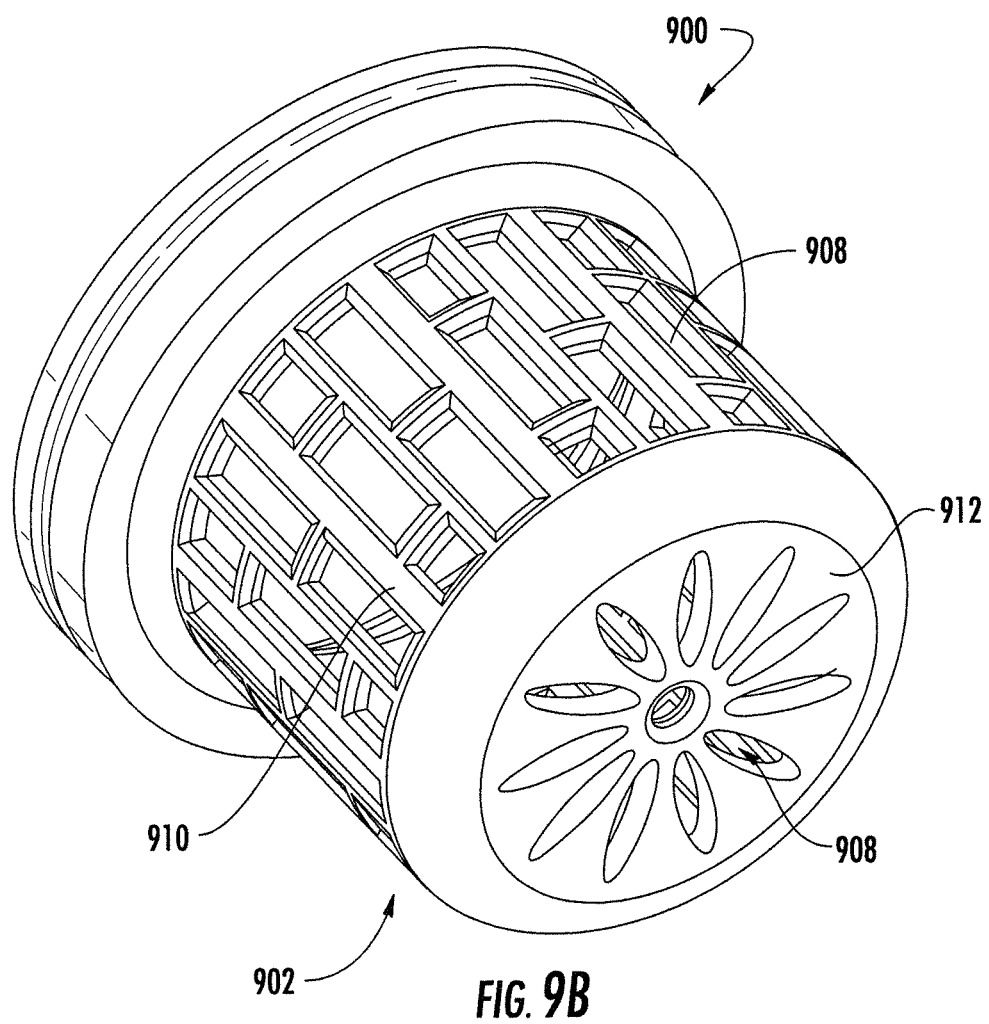

FIGS. 9A and 9B depict other configurations of baskets 900. As with the embodiment depicted in FIGS. 8A and 8B, openings 908 penetrate the sidewall 910 and bottom wall 912 of the container portion 902. As clear from the figures, the openings 908 may be of any size or shape. Other basket shapes are contemplated. For example, the baskets may be shaped complementary to the shape of the well (i.e., round baskets and wells, square baskets and wells, etc.). In fact, the shape of both the basket and well may be configured as required or desired for a particular application.

Figure 10:
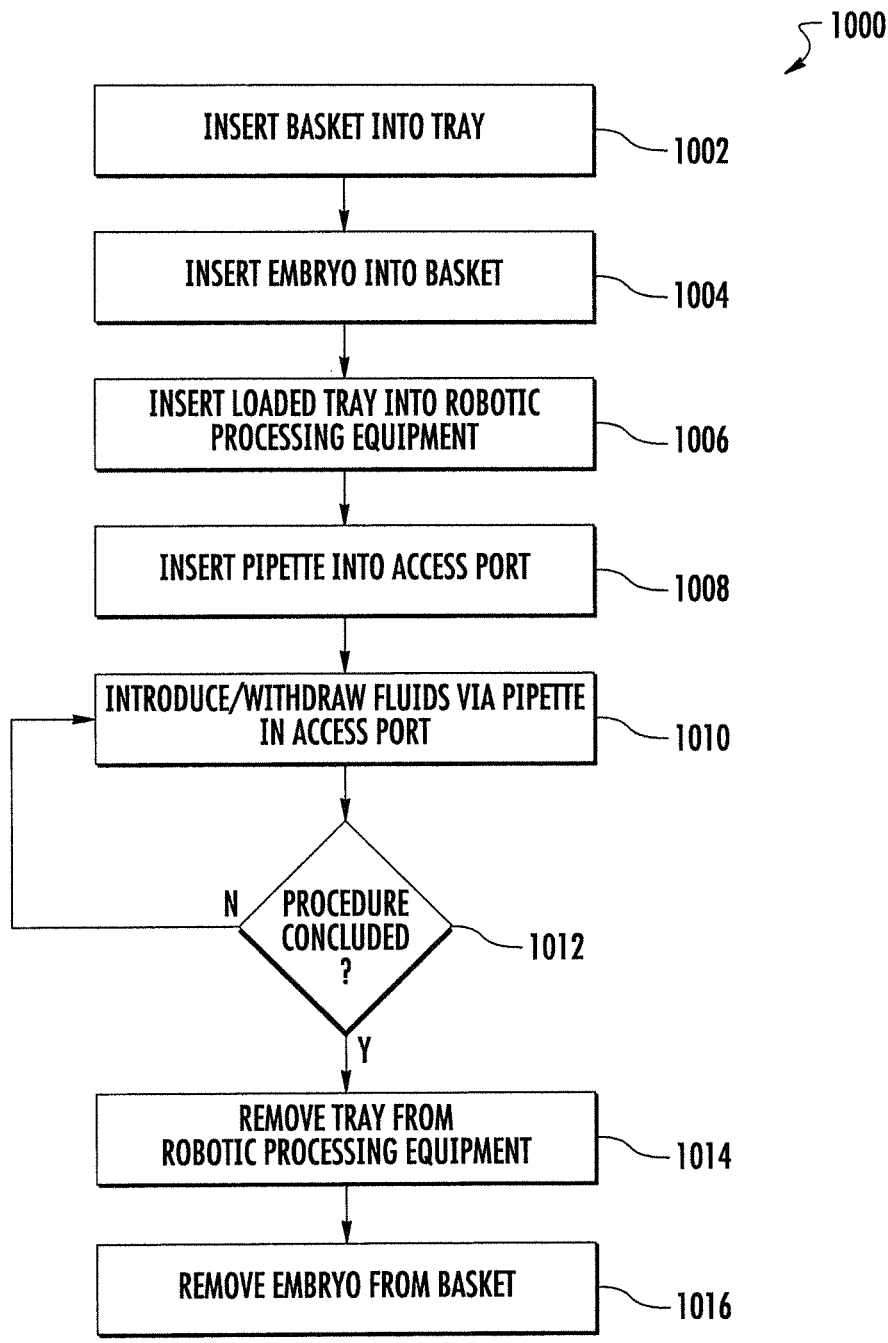
FIG. 10 depicts one method of using a tray and basket system for robotic processing of samples.

FIG. 10 depicts a method 1000 of utilizing a tray and basket system for biological sample processing, specifically, automatic robotic processing of embryos, including staining of the embryos. In operation 1002, the tray is loaded with one or more baskets by first inserting a basket into each well of the tray. This may be done manually by a technician, or may be performed by an appropriately-configured piece of robotic equipment. It may also be advantageous to insert the baskets into the wells during manufacture and assembly. The tray and basket system may then be appropriately sealed so as to avoid contamination and shipped to an end-user. After the baskets are loaded, or after the contaminant seal has been removed, an embryo may then be loaded into one or more baskets, as in operation 1004. Due to the delicate nature of the embryos, this is often performed by a human operator, although robotic equipment may be used. Once embryos have been inserted into the appropriate baskets, each loaded tray is then inserted into the robotic processing equipment, in operation 1006. The specific operations are programmed into the processing equipment or laboratory management software and are performed as required or desired for a particular application. During processing, regardless of the type of liquid introduced, the construction of the tray and basket system described herein allows the pipette to introduce or withdraw liquid without damaging or removing the embryo, or without the basket becoming dislodged from the tray. By inserting the pipette into the access port, as in operation 1008, damage to the embryo or removal of the embryo from the basket is eliminated. In operation 1010, fluid is introduced and withdrawn from the well via the access port. This procedure may be repeated as required for a particular process. The program used to control the robotic equipment will continue to perform the appropriate procedure, operation 1012, until concluded. Thereafter, as indicated at operation 1014, the tray is removed from the robotic processing equipment. A human operator or specialized robotic equipment may then remove the embryo as indicated in operation 1016.

Returning to operation 1010, an exemplary whole embryo processing protocol is provided below. As indicated above, the fluids are introduced and withdrawn via the access port to reduce the likelihood of damage to or removal of the embryo. Processes can be adapted for any specimens that can be retained in wells such as vibratome or sliding microtome-derived tissue slices, whole or partial preparations of embryonic or adult organs or tissues, etc.

Whole Mouse Embryo Processing Protocol
   A. Module W1, day 1
     i. Mount mouse embryos in Robot—begin Run
     ii. Immerse embryos in 2% Glutaraldehyde/paraformaldehyde (60 mins).
     iii. Immerse embryos in PBS (5 mins).
     iv. Immerse embryos 4× in PBS, (15 mins). E.g., 3× 10 mins with agitation
     v. Immerse embryos in LacZ staining solution
     vi. Remove embryos from Robot
       (1) Incubate slides at 4° C. 12-48 hours
       (2) Time and temperature of incubation varies
   B. Module W2, day 3
     i. Return Embryos to Robot
     ii. Immerse embryos 3× in PBS (5 mins each).
     iii. Immerse embryos in 2% paraformaldehyde
     iv. Remove embryos from Robot
       (1) Incubate 12 hrs
   C. Module W3, day 4
     i. Return Embryos to Robot
     ii. Immerse embryos 3× in PBS (15 mins).
     iii. Immerse embryos in 50% glycerol
     iv. Remove embryos from Robot
       (1) Incubate 12 hrs
   D. Module W4, day 5
     i. Return Embryos to Robot
     ii. Immerse embryos in 70% glycerol (12 hours)
     iii. Remove embryos from Robot iv. Transfer embryos to storage The tray system depicted herein is useful in many other biological processes where fluids must be added or withdrawn from a well, without damaging or inadvertently removing the sample with the suction created by the pipette. This may include other types of histochemistry, in-situ hybridization, or immuno-histochemistry. For example, samples within the well can include any suspended tissue or cell culture colonies, including plant or animal cells or tissues. In some embodiments, the samples are grown onto slides and the tray system is configured to hold the slide. In some embodiments, the samples are placed on the slide using a centrifuge or other known technique, and the tray system configured to hold the slide is used in a staining process. Regardless of the biological process in which tray and basket systems are used, the trays are typically configured to be similar or identical in outside dimensional size (length, width, thickness) to a standard microtiter plate. This allows the basket and tray system to be used easily with existing laboratory robotic processing systems.

Figure 11:
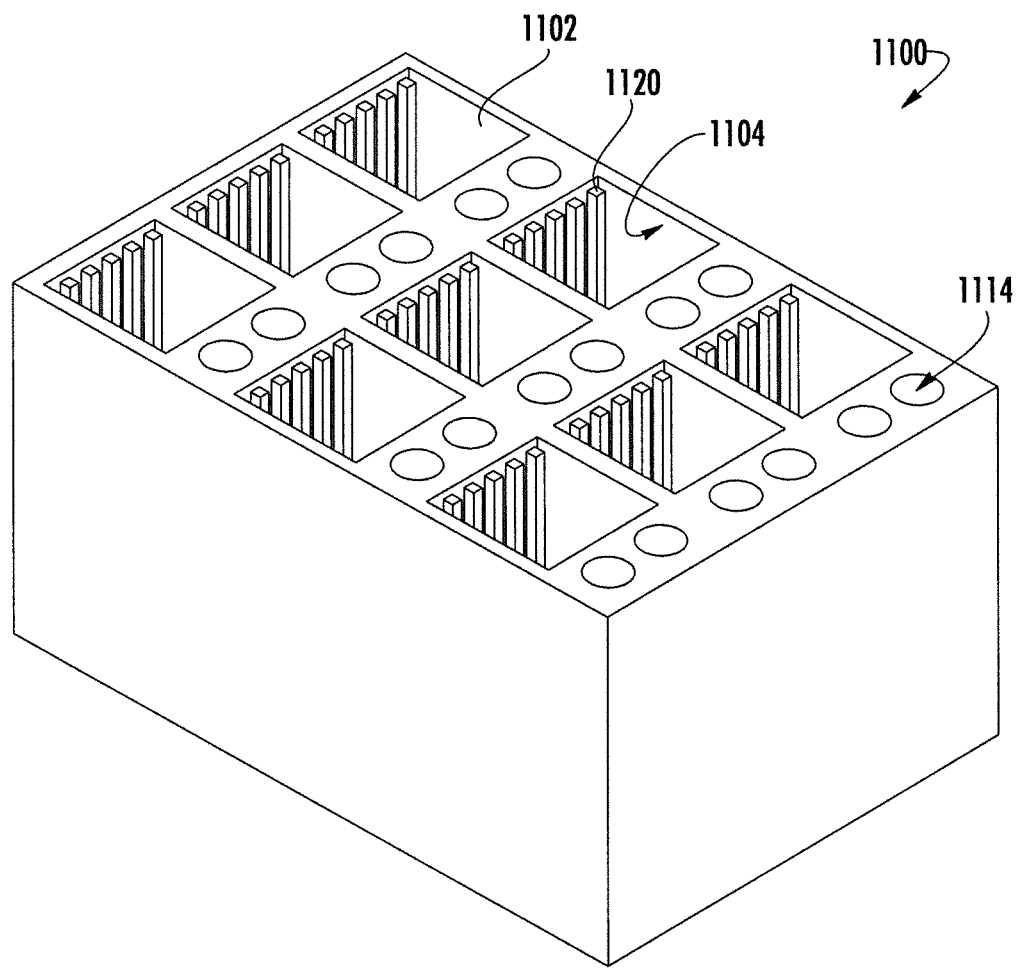
FIG. 11 depicts a top perspective view of a tray for use in processing slides.

FIG. 11 depicts a tray 1100 for processing a plurality of slides. The tray includes a number of wells 1102, each having a plurality of side walls 1104 and a bottom surface (not shown). Access ports 1114 (in this case, two associated with each well 1102) penetrate a top surface of the tray 1100. The access ports 1114 may be in fluidic communication with the wells 1102 in the same manner as depicted in the previous figures. That is, the access ports 1114 may be entirely discrete from the wells, as shown here and as depicted in FIG. 3A. In other embodiments, the access ports may be in fluidic communication with the wells via a drain and/or channel in the bottom surface, and/or slot in the side wall 1104. One or more walls 1104 (typically opposite-facing walls) of each well 1102 at least partially define a number of projections 1120. Adjacent projections 1120 are spaced so as to receive a slide therebetween. Any number of slides may be held in a particular well 1102, and the slides may be oriented such that the longitudinal axis of the slide is substantially vertical (as depicted) or horizontal. In the depicted embodiment, baskets need not be used, but in other embodiments, slides may be mounted in appropriately configured baskets, then the baskets may be inserted into the wells.

An exemplary slide processing system is depicted below.

Slide Processing Protocol

A. Mount Slides in Robot—begin Run (module S1 day 1)
B. Immerse slides in 2% paraformaldehyde for (5 mins)
C. Immerse slides in PBS (5 mins)
D. Immerse slides 4× in PBS, (10 mins)
E. Immerse slides in Lac Z staining solution.
F. Remove slides from Robot
  i. Incubate slides at 37 C overnight
  ii. Allow slides to return to RT
G. Return Slides to Robot (module S2 day 2)
H. Immerse slides 3× in PBS (5 mins each)
I. Immerse in 2% paraformaldehyde (60 mins)
J. Immerse slides 3× in PBS (10 mins)
  i. Immerse slides in Neutral Red (3 mins)
K. Immerse slides in D H2O (10 sec)
L. Immerse slides in 70% ethanol (5 mins)
M. Immerse slides in 85% ethanol (5 mins)
N. Immerse slides in 95% ethanol (5 mins)
O. Immerse slides 2× in 100% ethanol (5 mins each)
P. Immerse slides in Ethanol/Histoclear (5 mins)
Q. Immerse slides 2× in Histoclear (5 mins each)
R. End Robot run, Hold slides In some aspects, the sample is a mouse embryo. In other aspects, the sample is a tissue. In still other aspects, the sample is a suspended cell culture colony. The samples described here are biologic in nature; however, any sample is contemplated herein, where the sample size is of a sufficient size to avoid movement through the holes, openings, or penetrations in the basket.

Materials utilized in the manufacture of the trays and baskets described therein may be similar to those used in existing robotic biologic processing systems. For example, plastic materials such as TEFLON, DELRYN, various grades of polypropylene, ABS, or PVC may be used. Metals such as aluminum, stainless steel, and titanium also may be utilized. Additionally, the tray and baskets described herein may be manufactured from standard materials utilized for three-dimensional printing. Subsequent to manufacture, the tray or basket may be treated with a chemical solution that melts the outer surface of the tray or basket, thus rendering it non-porous. This process may be particularly useful for very complex tray or basket configurations.

It is contemplated herein that the baskets can be treated or untreated. For example, a treated basket may be capable of releasing growth factors or cytokines to facilitate growth of the tissues or cells within the basket.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the technology. Accordingly, what is desired to be secured by Letters Patent is the technology as defined and differentiated in the following claims, and all equivalents.

What is claimed is:

1. A system for processing samples by a robotic platform, the system comprising:
  a tray defining:
    a well defining a drain, wherein the well comprises a bottom surface; and
    an access port in fluid communication with the drain; and
  an insert adapted to be received in the well, wherein the insert comprises a bottom wall and a side wall, wherein both the bottom wall and the side wall separately define a plurality of openings, such that an interior of the insert is in fluid communication with the well when the insert is inserted into the well, and wherein at least some of the openings define an angle relative to the side wall or the bottom wall so as to induce a current or swirl in the fluid.

2. The system of claim 1, wherein the well defines a channel connecting the drain and the access port, wherein the channel is pitched downward from the drain to the access port.

3. The system of claim 2, wherein the bottom surface defines a top surface of the channel.

4. The system of claim 2, wherein the bottom surface at least partially defines an edge of the channel.

5. The system of claim 1, wherein the bottom surface defines the drain.

6. The system of claim 1, wherein the bottom surface comprises a high point and a low point, and wherein the drain is located proximate the low point.

7. The system of claim 6, wherein the low point is located proximate a center of the bottom surface.

8. The system of claim 6, wherein the low point is located proximate an outer edge of the bottom surface.

9. The system of claim 6, wherein the well comprises an outer wall, and wherein the outer wall at least partially defines the drain.

10. The system of claim 1, wherein the tray defines a slot, wherein the slot provides fluid communication between the well and the access port.

11. The system of claim 10, wherein the slot is configured to receive a gate.

12. The system of claim 1, wherein the well comprises an outer wall, and wherein when inserted into the well, the basket forms an interference fit with the outer wall.

13. The system of claim 12, wherein at least one of the outer wall and the basket comprises a gasket, wherein the gasket forms the interference fit.

14. The system of claim 1, wherein the tray further comprises at least one of a clamp or a latch for securing the basket within the well.

15. The system of claim 1, wherein the well comprises an outer wall, wherein the outer wall defines at least one of a circular shape, a quadrilateral shape, an oval shape, and a triangular shape.

16. The system of claim 15, wherein the side wall of the basket defines a shape complementary to the outer wall shape.

17. The system of claim 1, wherein the tray defines a plurality of wells and wherein the access port is in fluid communication with at least two of the plurality of wells.

18. The system of claim 1, wherein at least one of the plurality of openings comprises a sharp corner.

19. A tray for processing samples by a robotic platform, the tray comprising:
a well defining a geometric shape having at least one outer wall and a bottom surface;
an access port discrete from and in fluid communication with the well; and
a basket configured to fit within the well, wherein the basket defines at least one side wall and a bottom wall, and wherein both the side wall and bottom wall separately define a plurality of openings, and wherein at least some of the openings define an angle relative to the side wall or the bottom wall so as to induce a current or swirl in the fluid.

20. The tray of claim 19, wherein the well defines a drain defined by at least one of the outer wall and the bottom surface.

21. The tray of claim 19, wherein the bottom surface is at least one of substantially convex and substantially concave.

22. The tray of claim 19, wherein the bottom surface is sloped toward the outer wall.

23. The tray of claim 19, wherein the tray further comprises a channel connecting the well to the access port, wherein the channel is located below the bottom surface.

24. The tray of claim 23, wherein the bottom surface at least partially defines the channel.

25. The tray of claim 19, wherein the tray comprises a plurality of wells and the access port is in fluid communication with at least two of the plurality of wells.

* * * * *